(12) United States Patent
Vanderby et al.

(10) Patent No.: US 7,736,315 B2
(45) Date of Patent: Jun. 15, 2010

(54) METHOD AND APPARATUS PROVIDING IMPROVED ULTRASONIC STRAIN MEASUREMENTS OF SOFT TISSUE

(75) Inventors: Ray Vanderby, Madison, WI (US); Hirohito Kobayashi, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 1102 days.

(21) Appl. No.: 11/192,930

(22) Filed: Jul. 29, 2005

(65) Prior Publication Data

US 2006/0025682 A1 Feb. 2, 2006

Related U.S. Application Data

(60) Provisional application No. 60/592,746, filed on Jul. 30, 2004.

(51) Int. Cl.
  A61B 8/00 (2006.01)
(52) U.S. Cl. .................. 600/438; 600/437; 600/442; 600/443
(58) Field of Classification Search ......... 600/437–438, 600/442, 443
See application file for complete search history.

(56) References Cited

U.S. PATENT DOCUMENTS

| | | | |
|---|---|---|---|
| 5,107,837 A | | 4/1992 | Ophir et al. |
| 5,265,612 A | | 11/1993 | Sarvazyan et al. |
| 5,293,870 A | * | 3/1994 | Ophir et al. ............. 600/437 |
| 5,524,636 A | | 6/1996 | Sarvazyan et al. |
| 5,785,663 A | * | 7/1998 | Sarvazyan ............... 600/587 |
| 5,922,018 A | * | 7/1999 | Sarvazyan ............... 600/587 |
| 6,508,768 B1 | * | 1/2003 | Hall et al. .............. 600/443 |
| 7,022,077 B2 | | 4/2006 | Mourad et al. |
| 7,257,244 B2 | * | 8/2007 | Miga ..................... 382/128 |
| 7,331,926 B2 | * | 2/2008 | Varghese et al. ......... 600/443 |

OTHER PUBLICATIONS

Takahashi et al., "Stress Dependency on the Ultrasonic Wave Velocity and Attenuation of Fe-C System," 1996, Journal De Physique IV, vol. 6, pp. C8845-C8848.*

MacDonald, Douglas, "On Determining Stress and Strain and Texture using Ultrasonic Velocity Measurements," 1981, IEEE Transactions on Sonics and Ultrasonics, vol. SU-28, No. 2, pp. 75-79.*

Prosser, William. "Stress Dependence of Ultrasonic Velocity in Unidirectional Graphite/Epoxy Composites for Longitudinal Waves Propagating Along the Direction of Stress." Review of Progress in Quantitative Nondestructive Evaluation. 1990. vol. 9. pp. 1701-1707.*

Ponnekanti H., Ophir, J., and Cespedes I., 1992, "Axial Stress Distributions Between Coaxial Compressor in Elastography: An Analytical Model", Ultrasound in Med. & Biol. vol. 18, No. 8, pp. 667-673.

Cespedes I., Ophir J., and Ponnekanti H., Maklad, N. 1993, "Elastography: Elasticity Imaging Using with Application to Muscle and Breast In Vivo", Ultrasonic Imaging, vol. 15, pp. 73-88.

(Continued)

*Primary Examiner*—Brian Casler
*Assistant Examiner*—James Kish
(74) *Attorney, Agent, or Firm*—Boyle Fredrickson, S.C.

(57) ABSTRACT

The variation in acoustic properties in soft tissues, such as biological tissues, as a function of strain may be modeled to improve elastographic measurements and to obtain direct measurements of strain or material properties and pre-stress.

26 Claims, 3 Drawing Sheets

OTHER PUBLICATIONS

PCT/USO5/27081, International Search Report.
PCT/US05/27081, Written Opinion of the International Search Authority.
Kish, James M., "Final Office Action" for U.S. Appl. No. 11/549,865, dated Aug. 4, 2009, Notice of References Cited, United States Patent and Trademark Office, Alexandria, VA, USA.
Hakulinen, M. A. et al., Ability of Ultrasound Backscattering to Predict Mechanical Properties of Bovine Trabecular Bone, Ultrasound in Medicine and Biology, pp. 919-927, Jul. 1, 2004, vol. 30, No. 7, Elsevier, New York, NY, USA.
Bengtsson, Johan, Supplementary European Search Report, Sep. 17, 2009, European Patent Office, The Hague, The Netherlands.

* cited by examiner

FIG. 8 ial Stress Distributions Between Coaxial Compressor in Elastography: An Analytical Model", *Ultrasound in Med. & Biol.*, Vol. 18, No. 8, pp. 667-673.

METHOD AND APPARATUS PROVIDING IMPROVED ULTRASONIC STRAIN MEASUREMENTS OF SOFT TISSUE

CROSS-REFERENCE TO RELATED APPLICATIONS

This application claims the benefit of U.S. Provisional Application 60/592,746 filed Jul. 30, 2004 hereby incorporated by reference.

STATEMENT REGARDING FEDERALLY SPONSORED RESEARCH OR DEVELOPMENT

This invention was made with United States government support awarded by the following agencies: NSF 9907977. The United States has certain rights in this invention.

BACKGROUND OF THE INVENTION

The present invention relates to ultrasonic medical imaging and quantitative measurements and, in particular, to an improved apparatus and method for making ultrasonic measurements of tissue strain and stiffness.

Conventional ultrasonic imaging provides a mapping of ultrasonic echo signals onto an image plane where the intensity of the echo, caused principally by differences in material properties between adjacent tissue types, is mapped to brightness of pixels on the image plane. While such images serve to distinguish structure within the body, they provide limited insight into the physical properties of the imaged materials.

Ultrasonic elastography is a new ultrasonic modality that may produce an image revealing stiffness properties of the tissue, for example, strain under an externally applied stress, Poisson's ratio, Young's modulus, and other common strain and strain-related measurements.

In one type of elastography, termed "quasi-static" elastography, two images of the tissue in two different states of compression, for example, no compression and a given positive compression, may be obtained by the ultrasound device. The tissue may be compressed by a probe (including the transducer itself) or by muscular action or movement of adjacent organs. Strain may be deduced from these two images by computing gradients of the relative shift of the tissue in the two images along the compression axis. Quasi-static elastography is analogous to a physician's palpation of tissue in which the physician determines stiffness by pressing the tissue and detecting the amount of tissue yield (strain) under this pressure.

The process of deducing the shift in tissue under compression may start by computing local correlations between the images and then evaluating differences in echo arrival time for correlated structures before and after compression. Differences in echo arrival time are converted to tissue displacement (or strain, which is displacement normalized by length) at different points within the tissue by multiplying the difference in arrival times by the speed of sound through the tissue.

The tissue strain indirectly provides an approximate measure of stiffness. Tissue that exhibits less strain under compression may be assumed to be stiffer while tissue that exhibits more strain under compression is assumed to be less stiff. This approximation, however, carries with it an assumption of a constant stress field, that is, that the force of compression is uniformly dispersed within the tissue. Generally this is not true, but rather the stress in an elastic body falls off as one moves away from the compressor and increases at stress concentrations near stiff inclusions.

Accordingly, it has been proposed to improve elastographic measurements by comparing the deduced strains against modeled stress fields produced by a finite size compressor in a semi-infinite homogeneous medium. See, for example, Ponnekanti H., Ophir, J., and Cespedes I., 1992, "Axial Stress Distributions Between Coaxial Compressor in Elastography: An Analytical Model", *Ultrasound in Med. & Biol.*, Vol. 18, No. 8, pp. 667-673.

A similar analytical model has been proposed for stress concentration near inclusions. See, Cespedes I., Ophir J., and Ponnekanti H., 1993, "Elastography: Elasticity Imaging Using Ultrasound with Application to Muscle and Breast In Vivo", *Ultrason. Imag.*, Vol. 15, pp. 73-88.

SUMMARY OF THE INVENTION

The present inventors have recognized that an implicit assumption of constant acoustic properties (sound speed or acoustic impedance or reflection coefficient) in current elastography measurements may be inappropriate for biological tissues in which material density, pre-stress, and stiffness (all of which affect sound speed and acoustic impedance and reflection coefficient) may all be a function of the strain. By improved modeling of acoustic property variations as a function of strain, an improved elastography measurement may be made (termed acoustoelastography herein).

The present invention also provides a new paradigm of strain measurement in soft tissue in which, rather than deducing tissue strain by measuring motion of the tissue under assumptions about stress fields and acoustic properties, strain is deduced directly from the modification of the ultrasonic signal caused by changes in the acoustic properties of the material. Similarly, if the strain is known, the material properties may be deduced.

Thus generally, the present invention exploits the recognition that strain in biological tissue fundamentally affects acoustic properties of biological tissues.

Specifically then, the present invention provides in a first embodiment, an ultrasonic elastography system having an ultrasonic transducer system adaptable to provide a set of echo signals from a plurality of voxels in a region of interest. The set of echo signals includes first echo signals taken of tissue of the region of interest in a first compressive state, and second echo signals taken of tissue in the region of interest in a second compressive state. A processor, operating according to a pre-determined program, models variations in acoustic properties of the tissue through the region of interest based upon changes in ultrasonic waves from the first to second compressive state. Strain at a plurality of voxels in the region of interest is then deduced from differences between the first and second echo signals as corrected by the modeled variation in acoustic properties, and the strain is used to compute elastic properties at the plurality of voxels from the determined strains.

Thus, it is one object of the invention to provide for improved elastographic measurements by recognizing significant variations in acoustic properties caused by compression of biological tissues.

The modeled variations in acoustic properties are produced by a generator function which may model one or more of: (i) a change in stiffness coefficient of the material of the region of interest with change in strain, (ii) changes in tissue density with changes in tissue strain, and (iii) changes in pre-stress with changes in tissue strain.

Thus, it is another object of the invention to provide a model which may flexibly incorporate multiple factors which may affect the acoustic properties within tissue.

The generator function may evaluate changes in acoustic properties at a plurality of voxels within the region of interest.

Thus, it is another object of the invention to provide a system suitable for correction or production of images.

The generator function may determine the strain at the plurality of voxels in the region of interest and use the strain to correct the modeled variation in acoustic properties.

Thus, it is another object of the invention to use the deduced strain to iteratively correct the acoustic properties as a function of stiffness, coefficient density, or pre-stress, each of which may be a function of strain.

The computation of elastic properties may also model a non-uniform variation in the stress through the region of interest caused by the change from the first to second compressive states in determining elastic properties.

Thus, it is another object of the invention to improve stiffness measurements of the tissue by more accurately modeling both acoustic properties variations and variation in the stress field from which such stiffness is computed.

The determined strains may be used to modify the modeled non-uniform variations in stress according to known non-linear characteristics of tissue.

Thus, it is another object of the invention to correct the stress modeling according to the actual measured strains and a priori knowledge of tissue non-linear stiffness.

In a second embodiment of the invention, the invention may provide an apparatus for measuring the strain in biological tissue and may have an ultrasonic transducer assembly for transmitting an incident ultrasonic waveform into the tissue, and obtaining a reflected ultrasonic waveform therefrom. A processor, operating according to a stored program, may compare the magnitude of the reflected and incident ultrasonic waveforms to determine a reflection coefficient, and the reflection coefficient may be applied to a mathematical model of the biological tissue to determine one of a strain of the tissue and material constants of the tissue when the other strain of the tissue and material constants of the tissue is known.

Thus, it is another object of the invention to exploit the functional relationship between material properties and acoustic properties, in this case, acoustic reflection, to directly deduce strain or material constants of the tissue without the need for measuring tissue dislocation.

The determined strain may be applied to a mathematical model of the biological tissue to determine a pre-stress of the tissue.

Thus, it is another object of the invention to provide a method of measuring in vivo pre-stress of tissue.

The determined strain may be strain of the tissue perpendicular to the propagation direction of the ultrasound waveform.

Thus, it is another object of the invention to provide a method of measuring strain lateral to the axis of ultrasound propagation, useful, for example, for the measurement of the Achilles tendon where axial propagation of ultrasound would be difficult.

It is another object of the invention to provide a method that may employ a single ultrasonic transducer on one side of the patient for measurement of stress and strain.

In an alternate embodiment, the present invention provides an apparatus for measuring strain in biological tissue having an ultrasonic transducer assembly for transmitting an incident ultrasonic waveform through the tissue and measuring the wave velocity of the ultrasonic waveform therethrough. A processor, operating according to a stored program, applies the wave velocity to a mathematical model of the biological tissue to determine one of the strain of the tissue and the material constants of the tissue when the other of strain of tissue and material constants of the tissue is known.

Thus, it is another object of the invention to provide a measurement technique that works with stronger transmitted rather than reflected ultrasonic signals.

These particular objects and advantages may apply to only some embodiments falling within the claims and thus do not define the scope of the invention.

DETAILED DESCRIPTION OF THE PREFERRED EMBODIMENT

I. Acoustoelastography

Figure 1:
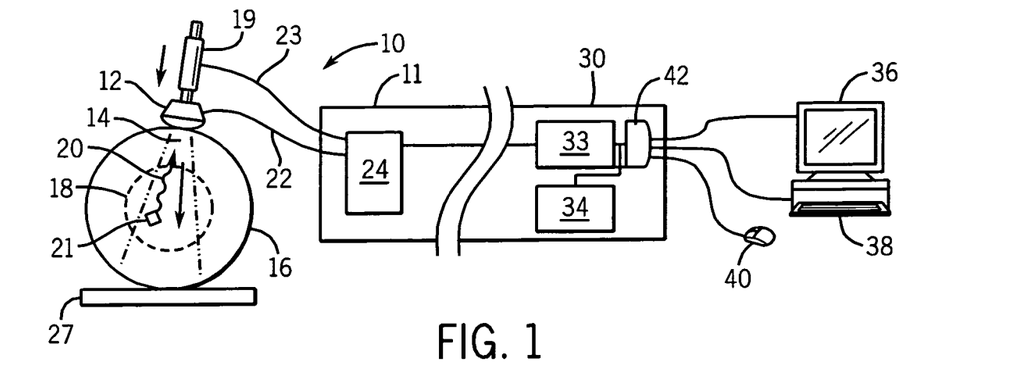
FIG. 1 is a simplified block diagram of an ultrasound scanner suitable for use with the present invention.

Referring now to FIG. 1, an acoustoelastographic imaging system 10 suitable for use with the present invention may employ an ultrasonic imaging machine 11 alone or in combination with an external computer 30. Generally, the ultrasonic imaging machine 11 provides the necessary hardware and/or software to collect and process ultrasonic echo signals by processor 33 held within the ultrasonic imaging machine 11 or in the external computer 30.

An ultrasonic transducer 12 associated with the ultrasonic imaging machine 11 may transmit an ultrasonic beam 14 toward a region of interest 18 within the patient 16 to produce echo signals 20 that may be received by the ultrasonic transducer 12 and converted to an electrical echo signal 22. For the construction of an image, multiple rays within ultrasonic beam 14 and echo signals 20 will be acquired through different voxels 21 in the patient so as to obtain an "echo set" of echo signals 20 from a plurality of voxels 21 within the region of interest 18.

The electrical echo signals 22 may be received by interface circuitry 24 of the ultrasonic imaging machine 11, the interface circuitry 24 providing amplification, digitization, and other signal processing as is understood in the art. The digitized echo signals may then be transmitted to a memory 34 for storage and subsequent processing by a processor 33 as will be described.

The processed echo signals 22 may be used to construct an image displayed on graphical display 36. Input commands from an operator may be received via a keyboard 38 or cursor control device 40, such as a mouse, attached to the processor 33 via interface 42 as is well understood in the art.

A position sensor 19 may be attached to the ultrasonic transducer 12 to indicate orientation of the ultrasonic transducer 12 and compression of the tissue of the patient 16 through an electrical position signal 23 also provided to the interface circuitry 24. A variety of different ultrasonic transducers 12 position determining mechanisms and methods for compression may be used in the present invention.

Figure 2:
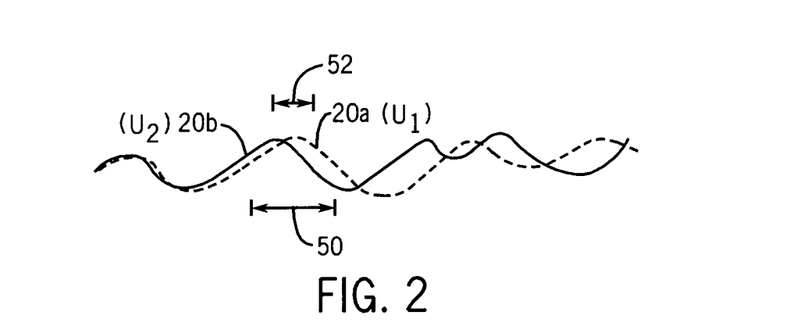
FIG. 2 is a plot of two ultrasonic echo signals from tissue in two compressive states, showing the determination of tissue displacement and strain under an assumption of constant ultrasound velocity.

Referring now to FIG. 2, a first echo set $U_1$ of signals including signal 20a may be acquired with a first degree of compression, for example, no compression applied to the ultrasonic transducer 12. A second echo set $U_2$ of signals including signal 20b may then be acquired with a first predetermined amount of compression from ultrasonic set. Compression as used herein should be understood to include negative compression, i.e. tension and other tissue displacing forces.

In a strain-determining step, a window 50 is established at successive locations along the waveforms 20a and 20b and a displacement distance 52 of points along the signals 20a and 20b is determined by a correlation of the waveforms 20a and 20b within the window 50. The derivative of these displacement distances 52 over the duration of the waveforms 20a and 20b provides an indication of the strain of the tissue at a particular voxel 21 with the patient 16 associated with the points on the waveforms. The windowing process may be performed in a number of ways including through use of the Fourier transform or auto correlation techniques well known in the art.

Figure 3:
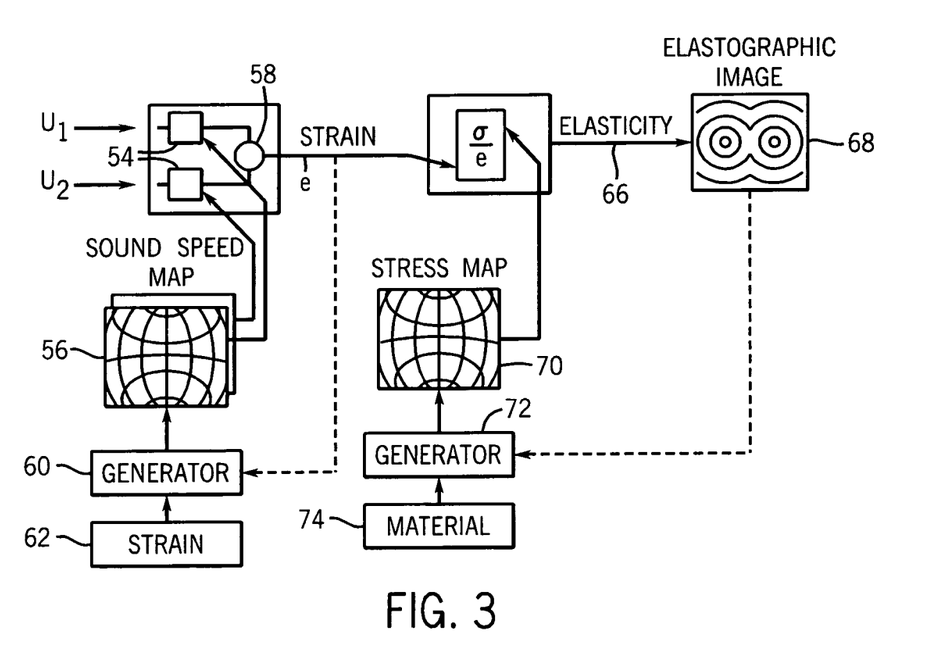
FIG. 3 is a signal flow diagram showing modification of the calculation of elasticity using an acoustic property map and stress field map to correct for variations in acoustic properties and stresses, the signal flow diagram as may be implemented in the scanner of FIG. 1 by the present invention.

Referring now to FIG. 3, accurate calculation of tissue displacement from the waveforms 20a and 20b requires accurate knowledge about acoustic properties through the tissue of the patient 16. These acoustic properties may vary in different tissues of the patient and may vary in each tissue depending on the local strain in the tissue. Accordingly in the present invention, each of the waveforms 20a and 20b of ultrasound sets $U_1$ and $U_2$ are first corrected as provided by corrector blocks 54 according to an acoustic property map 56 describing the acoustic property through each voxel of the region of interest 18.

The corrector blocks 54 expands or contracts the time scale of the waveforms 20a and 20b according to the relative acoustic property and known position of the ultrasonic transducer. So for portions of the acoustic property map 56 having a higher acoustic property (for example sound speed), the corresponding portion of the waveforms 20a and 20b crossing those portions are dilated to reflect the fact that the waveforms traverse a greater distance within the region of interest in a given time, and where the acoustic property is relatively lower, the corresponding portion waveforms is contracted similarly. As shown, different acoustic property maps 56 are used for the waveform 20a and 20b reflecting the fact that acoustic property is affected by the compression.

The corrected versions of waveforms 20a and 20b providing sets $U_1$ and $U_2$ are then correlated per block 58 to produce strain value e per methods understood in the art and as described above with respect to FIG. 2.

Referring still to FIG. 3, the acoustic property map is provided by a generator function 60 being a mathematical model, for example, $$V(x) = \sqrt{\frac{\tilde{C}_{11}(e(x)) + t^i_{11}(e(x))}{\rho(e(x))}}$$

where:

V(x) is the sound speed (an acoustic property) at a voxel defined at location x along the direction of ultrasound propagation;

$\tilde{C}_{11}$ is a stiffness of the tissue being a function of strain e at locations x along the direction of ultrasound propagation;

$t_{11}{}^i$ is a pre-stress of the tissue being a function of strain e at locations x along the direction of ultrasound propagation; and $\rho$ is a density of the tissue being a function of strain e at locations x along the direction of ultrasound propagation.

The functions $\tilde{C}_{11}, t_{11}{}^i$ and $\rho$ may be assumed to be homogenous through the region of interest and can be derived empirically through tests of ex vitro tissue and functionally approximated by a limited order, polynomial based this empirical data or captured in a look-up table. Initial strain values for these functions may be provided by a strain model 62 which may be initially prepared using an analytical model of strain fall off in a uniform body with known compression provided by information from the position sensor 19. This model of strain can be made using the analytical stress models described above and known in the prior art. In the first example, the strain model will generally show a strain fall-off as one moves away from the boundaries of the ultrasonic transducer 12 and table 27 reflecting a stress fall-off.

Once a value of strain e has been determined by process block 58, that value may be iteratively provided to the generator function 60 to improve the acoustic property map. Other refinements can also be contemplated including tissue differentiation based on a B-mode ultrasound image generated according to standard techniques known in the art.

The provided strain value may be given to an elasticity-computing block 64, essentially dividing the stress at any given voxel by the strain determined to be at that voxel to produce an elasticity value 66. The elasticity value 66 in turn may be used to produce an elastographic image 68.

In the simplest embodiment of the invention, the stress value for each voxel is assumed to be a constant over the region of interest 18 per prior art elastographic procedures. However in a preferred embodiment, a stress map 70 is used to provide the values of stress for process block 64. The stress map 70 may be produced by a generator 72 using analytical techniques such as those described in the prior art and based on known size of the compressor (here the ultrasonic transducer 12) its motion and position, and the position of the supporting table 27 for a material model 74 of composition of an average patient 16. Generally, the material model 74 used by the generator 72 will model a uniform material, however, this material model 74 may be refined by the elastographic image itself 68 to the extent that there may be inclusions of different stiffness properties that would cause a stress focusing.

By accommodating the variation in acoustic properties caused by functional dependence in the coefficients of the material, the pre-stress, and the density of the material as a function of strain, improved elastographic images can be obtained.

II. Acoustoelastic Strain Gauge

The relationship between the acoustic properties of tissue and strain allow strain to be determined without the intermediate step of measuring tissue displacement.

Figure 4:
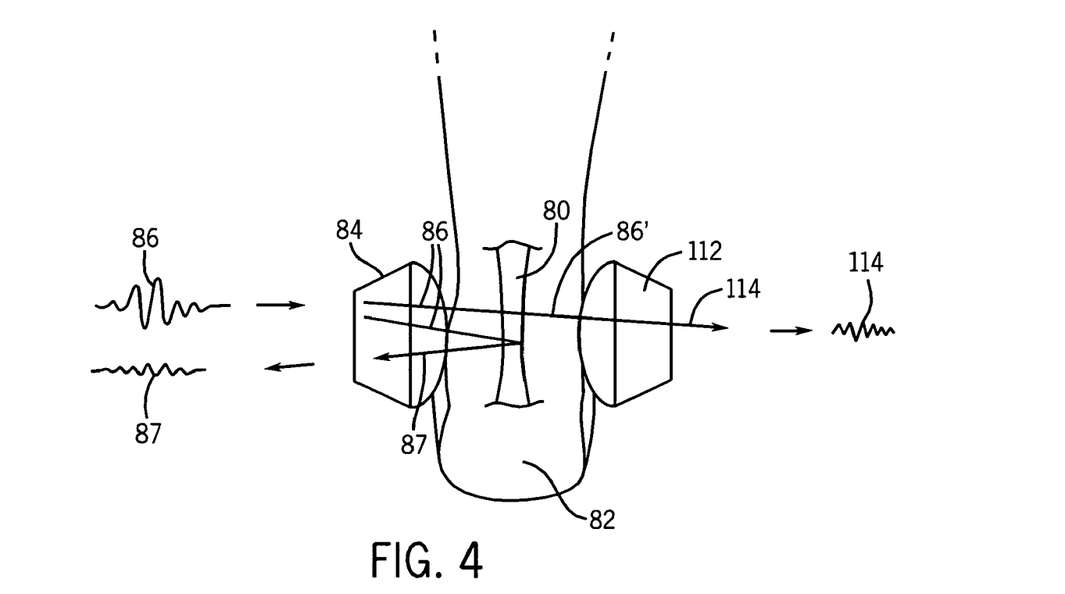
FIG. 4 is an elevational view of a person's lower leg showing the positioning of ultrasonic transducers for transmissive or reflective measurements of tissue such as the Achilles tendon in an alternative embodiment of the present invention.

Referring now to FIG. 4, measurement of strain in the Achilles tendon 80 in the human heel 82 may be made by placing an ultrasonic transducer 84 against the side of the heel 82 to transmit an incident waveform 86 into the tendon 80 and to receive an echo waveform 87 therefrom, the amount of echo being generally determined by changes in the acoustic properties of the tendon tissue versus the surrounding tissue of the heel 82.

Figure 5:
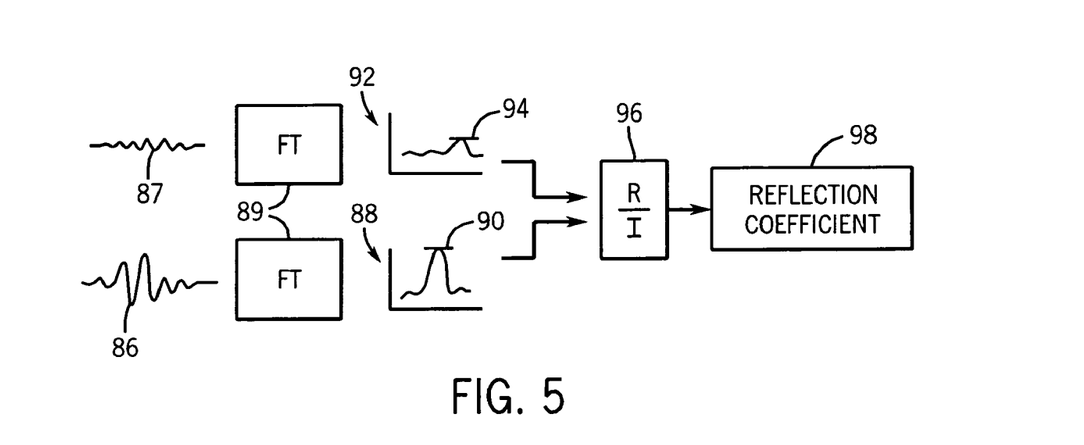
FIG. 5 is a representation of the calculation of a reflection coefficient when a single transducer is used in the embodiment of FIG. 4.

As shown in FIG. 5, the incident waveform 86 may be processed by the Fourier transform to produce a spectrum 88 from which a peak amplitude 90 may be determined, being the amplitude of the highest amplitude frequency component of the spectrum 88. Likewise, the echo waveform 87 may be processed by the Fourier transform indicated by block 89 to produce spectrum 92, providing a peak amplitude 94, being the amplitude of the highest amplitude frequency component of the spectrum 92.

A ratio of these two peak amplitude values 90 and 94 (the peak amplitude 94 divided by the peak amplitude 90) taken by process block 96 provides a reflection coefficient 98 that is a function of strain e.

Figure 7:
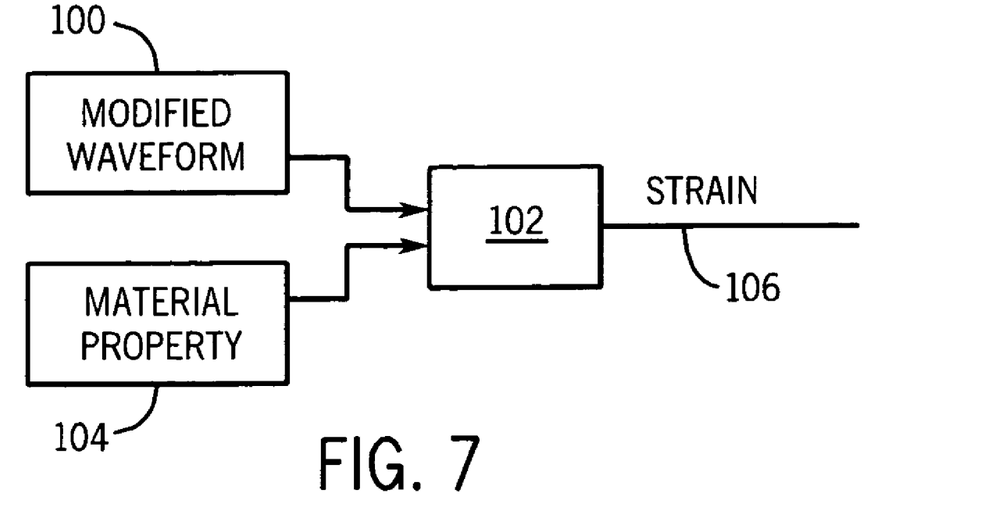
FIG. 7 is a representation of a forward calculation possible with the present invention where pre-stress is deduced from a reflection coefficient and the material properties.

The reflection coefficient 98 may be used in two ways. One way is to use the reflection coefficient to solve the "forward problem" as shown in FIG. 7. Here, the reflection coefficient 98 provides the information of a modified waveform 100 (modified by reflection) that is applied to a mathematical model 102 that related the modification of the waveform and known material properties 104 to a value of the strain 106.

One mathematical model 102 is:

$$4C_1 + 4C_2 + 2C_3 + (4C_1 + 4C_2 + 2C_3 + 6C_4)\frac{e}{1+e}$$

$$\frac{(1+e)(C_1 + C_2 + C_1 e - C_2 e - C_2 e^2)}{C_1 + C_2 + C_3 + 2C_1 e - 2C_3 e - C_1 e^2 + C_3 e^2} = \frac{1}{\rho^S}\left[\frac{(1+R)}{(1-R)}\rho^W v_D^W\right]^2$$

where $C_1$, $C_2$, $C_3$, and $C_4$ are known material constants,
e is the strain to be determined,
R is the reflection coefficient,
$\rho^S$, and $\rho^W$ are the densities of solid tissue and water, respectively, and
$v_D^W$ is the velocity of a dilatational wave in water.

The strain 106 of the tissue may then be applied to a model of the known material properties to yield a pre-stress value. One model is:

$$t_{11}^i(e) = 2C_1(1+e)^2 - (2C_1 + 4C_2) +$$

$$4C_2(1+e) + b(e)\left[\frac{2e(C_4 + 2C_2 e)}{1+e} - 2C_1 e(1+e) - \right.$$

$$\left. \frac{2e(C_1 + C_3)}{1+e} + \frac{2(2C_1 + 2C_2 + C_3)}{1+e} - 4C_2\right]$$

where $t_{11}^i$ is the pre-stress to be determined,
$C_1$, $C_2$, and $C_3$ are known material constants,
e is the determined strain, and b is dimensional shrinkage modeled as $$\frac{(1+e)(C_1 + C_2 + C_1 e - C_2 e - C_2 e^2)}{C_1 + C_2 + C_3 + 2C_1 e - 2C_3 e - C_1 e^2 + C_3 e^2}$$

being a function of strain e.

Figure 8:
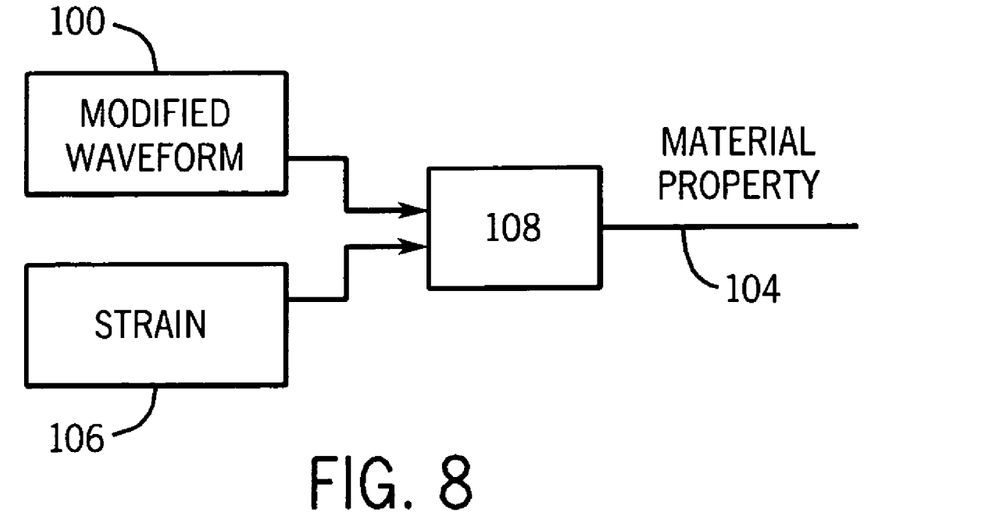
FIG. 8 is a representation of a backward or inverse calculation possible with the present invention where material properties are deduced from reflection coefficient and known pre-strain.

The reflection coefficient 98 may instead be used to solve the "inverse problem" as shown in FIG. 8. Here, the reflection coefficient 98 again provides the information of a modified waveform 100 (modified by reflection) that is applied to a mathematical model 108 that related the modification of the waveform and known strain 106, to values of the material properties 104. In this inverse problem, a number of different material properties 104 reflected in different coefficients must be produced and, therefore, multiple independent measurements of a modified waveform 100 at different pre-strains 106 must be made. A mathematical model 108 that may be used for this purpose is a set of simultaneous equations:

$$4C_1 + 4C_2 + 2C_3 + (4C_1 + 4C_2 + 2C_3 + 6C_4)\frac{e}{1+e}$$

$$\frac{(1+e)(C_1 + C_2 + C_1 e - C_2 e - C_2 e^2)}{C_1 + C_2 + C_3 + 2C_1 e - 2C_3 e - C_1 e^2 + C_3 e^2} = \frac{1}{\rho^S}\left[\frac{(1+R_1)}{(1-R_1)}\rho^W v_D^W\right]^2$$

$$4C_1 + 4C_2 + 2C_3 + (4C_1 + 4C_2 + 2C_3 + 6C_4)\frac{e}{1+e}$$

$$\frac{(1+e)(C_1 + C_2 + C_1 e - C_2 e - C_2 e^2)}{C_1 + C_2 + C_3 + 2C_1 e - 2C_3 e - C_1 e^2 + C_3 e^2} = \frac{1}{\rho^S}\left[\frac{(1+R_2)}{(1-R_2)}\rho^W v_D^W\right]^2$$

$$4C_1 + 4C_2 + 2C_3 + (4C_1 + 4C_2 + 2C_3 + 6C_4)\frac{e}{1+e}$$

$$\frac{(1+e)(C_1 + C_2 + C_1 e - C_2 e - C_2 e^2)}{C_1 + C_2 + C_3 + 2C_1 e - 2C_3 e - C_1 e^2 + C_3 e^2} = \frac{1}{\rho^S}\left[\frac{(1+R_3)}{(1-R_3)}\rho^W v_D^W\right]^2$$

$$4C_1 + 4C_2 + 2C_3 + (4C_1 + 4C_2 + 2C_3 + 6C_4)\frac{e}{1+e}$$

$$\frac{(1+e)(C_1 + C_2 + C_1 e - C_2 e - C_2 e^2)}{C_1 + C_2 + C_3 + 2C_1 e - 2C_3 e - C_1 e^2 + C_3 e^2} = \frac{1}{\rho^S}\left[\frac{(1+R_4)}{(1-R_4)}\rho^W v_D^W\right]^2$$

where $R_1$, $R_2$, $R_3$ and $R_4$ are reflection coefficients taken at different levels of tissue stress,
where $C_1$, $C_2$, $C_3$, and $C_4$ are the material constants to be determined,
e is the known strain,
$\rho^S$, and $\rho^W$ are the densities of solid tissue and water, respectively, and
$v_D^W$ is the velocity of a dilatational wave in water.

Referring again to FIG. 4, in an alternative embodiment, the ultrasonic transducer 84 may provide an incident waveform 86' that passes through the heel 82 and tendon 80 to be received by a second ultrasonic transducer 112 as a received waveform 114.

Figure 6:
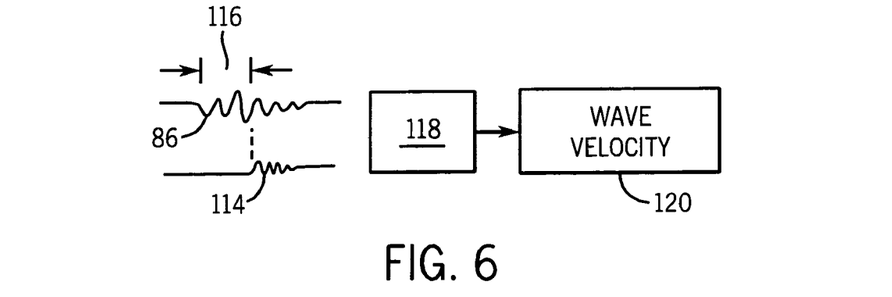
FIG. 6 is a representation of the calculation of a wave velocity when two ultrasonic transducers are used in the embodiment of FIG. 4.

Referring to FIG. 6, the delay 116 in phase between the incident waveform 86 and the received waveform 114 may then be measured by delay block 118 to produce a wave velocity value 120, being essentially the velocity of the wave through the heel 82 and tendon 80 corrected by changes in the thickness of the tendon and the intervening or surrounding tissue.

The wave velocity value 120, like the reflection coefficient 98 described above, may be used in either the forward problem as the modified waveform 100 shown in FIG. 7 or the inverse problem shown in FIG. 8, according to the following equations.

The mathematical model 102 for the forward problem may be:

$$C_{yy} = \sqrt{\frac{\tilde{C}_{22}}{\rho}}$$

$$\tilde{C}_{22} = 4C_1 + 4C_2 + 2C_3 + (4C_1 + 4C_2 + 2C_3 + 6C_4)\frac{be}{1+e}$$

$c_{yy}$ is the measured wave velocity,
where $C_1$, $C_2$, $C_3$, and $C_4$ are known material constants,
e is the strain to be determined, and
$\rho$ is the density of the tissue.

As before, the strain 106 of the tissue may then be applied to a model of the known material properties to yield a pre-stress value using the model described above.

Again, the reverse mathematical model 108 requires a set of simultaneous equations, in this case:

$$c_1 = \sqrt{\frac{\tilde{C}_1}{\rho}}$$

$$\tilde{C}_1 = 4C_1 + 4C_2 + 2C_3 + (4C_1 + 4C_2 + 2C_3 + 6C_4)\frac{be}{1+e}$$

$$c_2 = \sqrt{\frac{\tilde{C}_2}{\rho}}$$

$$\tilde{C}_2 = 4C_1 + 4C_2 + 2C_3 + (4C_1 + 4C_2 + 2C_3 + 6C_4)\frac{be}{1+e}$$

$$c_3 = \sqrt{\frac{\tilde{C}_3}{\rho}}$$

$$\tilde{C}_3 = 4C_1 + 4C_2 + 2C_3 + (4C_1 + 4C_2 + 2C_3 + 6C_4)\frac{be}{1+e}$$

$$c_1 = \sqrt{\frac{\tilde{C}_1}{\rho}}$$

$$\tilde{C}_1 = 4C_1 + 4C_2 + 2C_3 + (4C_1 + 4C_2 + 2C_3 + 6C_4)\frac{be}{1+e}$$

$$c_4 = \sqrt{\frac{\tilde{C}_4}{\rho}}$$

$$\tilde{C}_4 = 4C_1 + 4C_2 + 2C_3 + (4C_1 + 4C_2 + 2C_3 + 6C_4)\frac{be}{1+e}$$

where $c_1$, $c_2$, $c_3$, and $c_4$, are waveform velocities taken at different levels of tissue stress.

In this way, strain can be directly determined from the modification of an ultrasonic waveform by the intervening tissue based on an understanding of the change in acoustic properties of tissue as a function of strain. The acoustoelastographic techniques described above can be repeated for different locations through the tendon to produce an image of strain or of material properties or of pre-stress.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ultrasonic acoustoelastography system comprising:
an ultrasonic transducer system adapted to provide a set of echo signals from a plurality of voxels in a region of interest of a material, the set of echo signals including first echo signals taken of tissue of the region of interest in a first compressive state and second echo signals taken of tissue of the region of interest in a second compressive state; and
a processor operating according to a predetermined program to:
(a) model variations in the acoustic property of the material in the region of interest as a function of strain;
(b) determine a corrected strain of a plurality of voxels in the region of interest from a measured strain derived from differences between the first and second echo signals by correcting the measured strain of the plurality of voxels by the modeled variations in acoustic property; the correction determining variations in acoustic property of the material from ultrasonic measurements of the region of interest; and
(c) compute elasticity at the plurality of voxels from the corrected strains.

2. The ultrasound acoustoelastography system of claim 1 wherein the modeled variations in acoustic property are produced by a generator function determining changes in stiffness coefficient of the material in the region of interest as a function of strain in the material in the region of interest.

3. The ultrasound acoustoelastography system of claim 2 wherein the generator function determines changes in stiffness coefficient as a function of strain at a plurality of voxels within the region of interest.

4. The ultrasound acoustoelastography system of claim 3 wherein the generator function receives the corrected strain at the plurality of voxels to iteratively correct the modeled variations in acoustic property.

5. The ultrasound acoustoelastography system of claim 1 wherein the modeled variations in acoustic property are produced by a generator function determining changes in tissue density as a function of tissue strain.

6. The ultrasound acoustoelastography system of claim 5 wherein the generator function determines changes in density as a function of tissue strain at a plurality of voxels within the region of interest.

7. The ultrasound acoustoelastography system of claim 6 wherein the generator function iteratively receives the strain at the plurality of voxels in the region of interest to correct the modeled variations in acoustic property.

8. The ultrasound acoustoelastography system of claim 1 wherein the modeled variations in acoustic property are produced by a generator function determining changes in applied stress as a function of tissue strain.

9. The ultrasound acoustoelastography system of claim 8 wherein the generator function determines changes in applied stress as a function of tissue strain as a function of location within the region of interest.

10. The ultrasound acoustoelastography system of claim 9 wherein the generator function receives the corrected strain at the plurality of voxels in the region of interest to iteratively correct the modeled variations in acoustic property.

11. The ultrasound acoustoelastography system of claim 1 wherein the modeled variations in acoustic property follow a function:

$$V(x) = \sqrt{\frac{\tilde{C}_{11}(e(x)) + \tilde{r}_{11}(e(x))}{\rho(e(x))}}$$

where:
V(x) is the acoustic property at a voxel defined at location x along the direction of ultrasound propagation;

$\tilde{C}_{11}$ is a stiffness of the tissue being a function of corrected strain e at locations x along the direction of ultrasound propagation;

$t_{11}{}^i$ is applied stress on the tissue being a function of corrected strain e at locations x along the direction of ultrasound propagation; and ρ is a density of the tissue being a function of corrected strain e at locations x along the direction of ultrasound propagation.

12. The ultrasound acoustoelastography system of claim 1 wherein the computation of elasticity models a non-uniform variation in the stress through the region of interest caused by the change from the first to second compressive state in determining the elasticity at the plurality of voxels from the corrected strain.

13. The ultrasound acoustoelastography system of claim 12 wherein the corrected strain is used to modify the modeled non-uniform variation in stress according to known non-linear characteristics of tissue.

14. A method of ultrasonic acoustoelastography comprising the steps of:
(a) collecting a set of echo signals from a plurality of voxels in a region of interest, the set of echo signals including first echo signals taken of tissue of the region of interest in a first compressive state and second echo signals taken of tissue of the region of interest in a second compressive state;
(b) modeling variations in the acoustic property of the material of the region of interest as a function of strain;
(c) determining a corrected strain of a plurality of voxels in the region of interest from a measured strain derived from differences between the first and second echo signals by correcting the measured strain of the plurality of voxels by the modeled variations in acoustic property, the correction determining variations in acoustic property from ultrasonic measurements of the region of interest; and
(d) computing elasticity at the plurality of voxels from the corrected strains.

15. The method of claim 14 wherein the modeled variations in acoustic property are produced by a generator function determining changes in stiffness coefficient as a function of tissue strain.

16. The method of claim 15 wherein the generator function determines changes in stiffness coefficient as a function of tissue strain as a function of location within the region of interest.

17. The method of claim 16 wherein the generator function iteratively receives the corrected strain at the plurality of voxels to correct the modeled variations in acoustic property.

18. The method of claim 14 wherein the modeled variations in acoustic property are produced by a generator function determining changes in tissue density as a function of tissue strain.

19. The method of claim 18 wherein the generator function determines changes in density as a function of tissue strain as a function of location within the region of interest.

20. The method of claim 19 wherein the generator function iteratively receives the corrected strain at the plurality of voxels in the region of interest determined from differences between the first and second echo signals as corrected by the modeled variations in acoustic property.

21. The method of claim 14 wherein the modeled variations in acoustic property are produced by a generator function determining changes in applied stress as a function of tissue strain.

22. The method of claim 21 wherein the generator function determines changes in applied stress as a function of corrected tissue strain as a function of location within the region of interest.

23. The method of claim 22 wherein the generator function receives the strain at the plurality of voxels in the region of interest to iteratively correct the modeled variations in acoustic property.

24. The method of claim 14 wherein the modeled variations in acoustic property employ a function:

$$V(x) = \sqrt{\frac{\tilde{C}_{11}(e(x)) + t_{11}^i(e(x))}{\rho(e(x))}}$$

where:

V(x) is the acoustic property at a voxel defined at location x along the direction of ultrasound propagation;

$\tilde{C}_{11}$ is a stiffness at points along the direction of ultrasound propagation being a function of corrected strain e at points x along the direction of ultrasound propagation;

$t_{11}{}^i$ is a pre-stress at points along the direction of ultrasound propagation being a function of corrected strain e at points x along the direction of ultrasound propagation; and ρ is a density at points along the direction of ultrasound propagation being a function of corrected strain e at points x along the direction of ultrasound propagation.

25. The method of claim 14 wherein the computation of elasticity models a non-uniform variation in the stress through the region of interest caused by the change from the first to second compressive state in determining the elasticity of the tissue at the plurality of voxels from the corrected strain.

26. The method of claim 25 wherein the corrected strain is used to modify the modeled non-uniform variation in stress according to known non-linear characteristics of tissue.

* * * * *